US010732245B2

(12) United States Patent
Noguchi et al.

(10) Patent No.: US 10,732,245 B2
(45) Date of Patent: Aug. 4, 2020

(54) DIAGNOSTIC IMAGING DEVICE AND IMAGE ACQUISITION METHOD

(71) Applicant: Hitachi, Ltd., Tokyo (JP)

(72) Inventors: Yoshimi Noguchi, Tokyo (JP);
Masahiro Ogino, Tokyo (JP); Takenori Murase, Tokyo (JP); Tetsuhiko Takahashi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 13 days.

(21) Appl. No.: 16/093,680

(22) PCT Filed: Apr. 12, 2017

(86) PCT No.: PCT/JP2017/014966
§ 371 (c)(1),
(2) Date: Oct. 15, 2018

(87) PCT Pub. No.: WO2017/203875
PCT Pub. Date: Nov. 30, 2017

(65) Prior Publication Data
US 2019/0137589 A1 May 9, 2019

(30) Foreign Application Priority Data

May 26, 2016 (JP) ................................. 2016-105023

(51) Int. Cl.
*A61B 6/00* (2006.01)
*G06T 5/00* (2006.01)
(Continued)

(52) U.S. Cl.
CPC .......... *G01R 33/5608* (2013.01); *A61B 5/055* (2013.01); *A61B 6/032* (2013.01);
(Continued)

(58) Field of Classification Search
CPC .............. A61B 6/00; G06T 5/00; G01R 33/56
(Continued)

(56) References Cited

U.S. PATENT DOCUMENTS 9,275,439 B2 * 3/2016 Miyamoto .............. G06T 5/003

FOREIGN PATENT DOCUMENTS

JP 2005-004506 A 1/2005
JP 2013-183834 A 9/2013

OTHER PUBLICATIONS

Japanese Office Action received in corresponding Japanese Application No. 2016-105023 dated Dec. 10, 2019.
(Continued)

*Primary Examiner* — Abolfazl Tabatabai
(74) *Attorney, Agent, or Firm* — Mattingly & Malur, PC

(57) ABSTRACT

In a diagnostic imaging device, such as an MRI device, correction processing improves an image to be a high-quality image and an imaging time is shortened. In the diagnostic imaging device, a noise reduction unit 201 reduces a noise in observation data acquired with an observation unit 100 and converted into an image, and the image correction unit 202 corrects the noise reduced data by correction processing that uses visual characteristics of human. The image correction unit 202 separates the noise reduced data into a broad luminance component and a local variation component, and generates a correction level map using the broad luminance component. Correcting the noise reduced data using this correction level map and the local variation component acquires a high-quality image that is competent in the clinical field.

14 Claims, 7 Drawing Sheets

(51) Int. Cl.
  *G01R 33/56* (2006.01)
  *A61B 5/055* (2006.01)
  *A61B 8/08* (2006.01)
  *A61B 6/03* (2006.01)
  *G01R 33/565* (2006.01)
  *G01R 33/54* (2006.01)

(52) U.S. Cl.
  CPC .......... *A61B 6/5205* (2013.01); *A61B 6/5258* (2013.01); *A61B 8/5207* (2013.01); *A61B 8/5269* (2013.01); *G01R 33/56* (2013.01); *G01R 33/56509* (2013.01); *G06T 5/002* (2013.01); *G06T 5/003* (2013.01); *G01R 33/546* (2013.01)

(58) Field of Classification Search
  USPC .......................................................... 382/131
  See application file for complete search history.

(56) References Cited

OTHER PUBLICATIONS

Tsujioka, K., "60.TV Algorithm as an Inerative Image Filter", Inner Vision, 2013, pp. 122-123, vol. 28, No. 5.

Hongqing Hu, et al., Magetic Resonance Image Enhancement based on Multiscale Retinex Algorithm, 2010 3rd International Conference on Biomedical Engineering and Informatics (BMEI 2010), vol. 1, pp. 345-348.

Zohair Al-Ameen, et al., A New Algorithm for Improving the Low Contrast of Computed Tomography Images Using Tuned Brightness Controlled Single-Scale Retinex, Scanning, 2015, vol. 37, No. 2, pp. 116-1125.

International Search Report of PCT/JP2017/014966 dated Jun. 20, 2017.

* cited by examiner

DIAGNOSTIC IMAGING DEVICE AND IMAGE ACQUISITION METHOD

TECHNICAL FIELD

The present invention relates to a diagnostic imaging device, and relates to a high-quality picture technology in image processing.

BACKGROUND ART

A Magnetic Resonance Imaging (MRI), one of the medical diagnostic imaging devices, is a method that uses a Nuclear Magnetic Resonance (NMR) phenomenon to convert information of a test object, such as a living body, into an image. While a sufficient resolution is necessary in order to accurately interpret a target site in a clinical field, an MRI device, in principle, has a problem that a Signal to Noise Ratio (SNR) decreases when the resolution is increased. Therefore, in a general MRI device, the SNR is improved by increasing the Number of EXcitations (NEX) of signals, which is the number of multiple imaging and adding an identical site, that is, an identical position. A prior art of such image processing includes, for example, PLT 1. PLT 1 discloses correction processing of an image using Retinex theory that uses visual characteristics.

CITATION LIST

Patent Literature

PLT 1: Japanese Patent Application Laid-Open No. 2005-4506

SUMMARY OF INVENTION

Technical Problem

Since the above-described NEX and imaging time are in a proportional relation, the increased NEX causes a problem of lengthening the imaging time. While it is necessary to reduce a noise in post-processing on observation data, which is acquired in imaging, to shorten the imaging time, reducing the noise also reduces an edge (outline) and a luminance difference (contrast), which are original signals. In PLT 1, while a plurality of blur filters is used for correction processing using the Retinex theory to achieve an adaptive correction, there are problems of a processing load and a long processing time.

The objects of the present invention are to solve the above-described problems and to provide a diagnostic imaging device and an image acquisition method that ensure maintaining an image quality and reducing a processing time with an MRI image having a decreased NEX.

Solution to Problem

In order to achieve the above-described objects, the present invention provides a diagnostic imaging device configured to include a noise reduction unit and an image correction unit. The noise reduction unit reduces a noise in observation data converted into an image. The image correction unit performs correction processing that uses visual characteristics of human on noise reduced data acquired with the noise reduction unit.

In order to achieve the above-described objects, the present invention provides a diagnostic imaging device configured to include a noise reduction unit, a separating unit, a correction level calculator, a correction processing unit, and a correction control unit. The noise reduction unit reduces a noise in observation data converted into an image. The separating unit separates a broad luminance component and a local variation component from the noise reduced data acquired with the noise reduction unit. The correction level calculator calculates a correction level using the observation data, the noise reduced data, and the broad luminance component. The correction processing unit performs a correction using the observation data, the local variation component, and the correction level. The correction control unit uses parameters at a time of an acquisition of the observation data to control the noise reduction unit, the correction level calculator, and the correction processing unit.

Furthermore, in order to achieve the above-described objects, the present invention provides an image acquisition method of a diagnostic imaging device. The method performs: noise reduction processing that reduces a noise from acquired observation data; separation processing that separates a broad luminance component and a local variation component from noise reduced data acquired in the noise reduction processing; correction level calculation processing that calculates a correction level using the observation data, the noise reduced data, and the broad luminance component; and correction processing that uses the observation data, the local variation component, and the correction level.

Advantageous Effects of Invention

The present invention ensures acquiring a high-quality image while shortening an imaging time in a diagnostic imaging device.

DESCRIPTION OF EMBODIMENTS

The following describes various kinds of embodiments of the present invention in accordance with the drawings.

Example 1

An example 1 is an example of a diagnostic imaging device configured to include a noise reduction unit that reduces a noise in observation data converted into an image and an image correction unit that performs correction processing that uses visual characteristics of human on noise reduced data acquired with the noise reduction unit, and an image acquisition method of a diagnostic imaging device that performs noise reduction processing that reduces a noise from acquired observation data, separation processing that separates a broad luminance component and a local variation component from noise reduced data acquired in the noise reduction processing, correction level calculation processing that calculates a correction level using the observation data, the noise reduced data, and the broad luminance component, and correction processing that uses the observation data, the local variation component, and the correction level.

Figure 1:
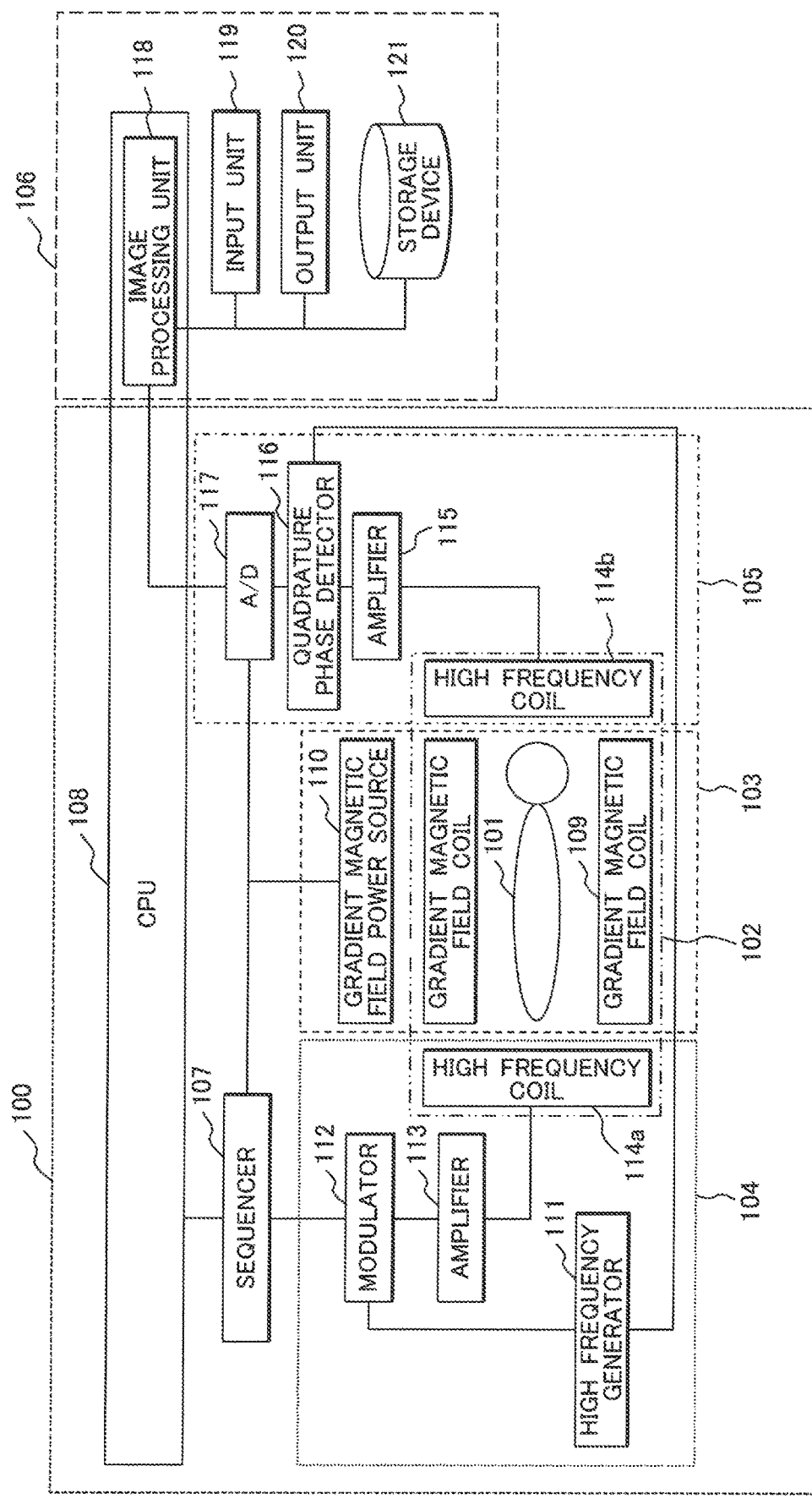
FIG. 1 is a drawing illustrating one example of an overall configuration of an MRI device according to each example.

FIG. 1 is a drawing illustrating one example of an overall configuration of an MRI device according to the example 1. As is apparent from FIG. 1, the MRI device as a medical diagnostic imaging device is roughly configured of an observation unit 100 and a reconfiguration unit 106. The observation unit 100 observes a test object and outputs observation data. The reconfiguration unit 106 reconfigures an image of the test object based on the observation data.

The observation unit 100 is configured of a static magnetic field generation system 102, a gradient magnetic field generation system 103, a transmission system 104, a reception system 105, a sequencer 107, and a central processing unit (CPU) 108. The static magnetic field generation system 102 generates a uniform magnetic field in a space around a test object 101. In order to generate the uniform magnetic field, in the static magnetic field generation system 102, a permanent magnet or magnetic field generation means of a normal conduction type or a superconductivity type is disposed. The gradient magnetic field generation system 103 is configured of a gradient magnetic field coil 109 and a gradient magnetic field power source 110 that drives the gradient magnetic field coil 109, and applies the gradient magnetic field to the test object 101.

The sequencer 107 is control means that repeatedly applies a high frequency magnetic field pulse (RF pulse) and a gradient magnetic field pulse at a predetermined pulse sequence. The sequencer 107 is operated by a control of the CPU 108, and transmits various kinds of instructions necessary for collecting tomographic image data of the test object 101 to the transmission system 104, the gradient magnetic field generation system 103, and the reception system 105. The transmission system 104 is configured of a high frequency generator 111, a modulator 112, an amplifier 113, and a high frequency coil 114a. The transmission system 104 emits the RF pulse that causes atomic nucleus spins of atoms, which constitute the test object 101, to develop a nuclear magnetic resonance. The reception system 105 is configured of a high frequency coil 114b, an amplifier 115, a quadrature phase detector 116, and an analog/digital (A/D) converter 117. The reception system 105 receives an echo signal emitted by the nuclear magnetic resonance of the atomic nucleus spins, and transmits the observation data to the reconfiguration unit 106.

The reconfiguration unit 106 is configured of an image processing unit 118, an input unit 119 that includes, for example, a keyboard, a computer mouse, a touchscreen, and a button, an output unit 120 that includes, for example, a display and a printer, and a storage device 121 that includes, for example, a magnetic disk and an optical disk and stores data and desired programs. When the reception system 105 inputs the observation data, the image processing unit 118 reconfigures an image and causes the output unit 120 to display the image, as well as recording the image in the storage device 121. As illustrated in FIG. 1, while this image processing unit 118 can be achieved by program processing by the CPU 108, it is also possible to install and use a central processing unit (CPU) different from the CPU 108 or configure and process using hardware dedicated for image processing in the reconfiguration unit 106.

Figure 2:
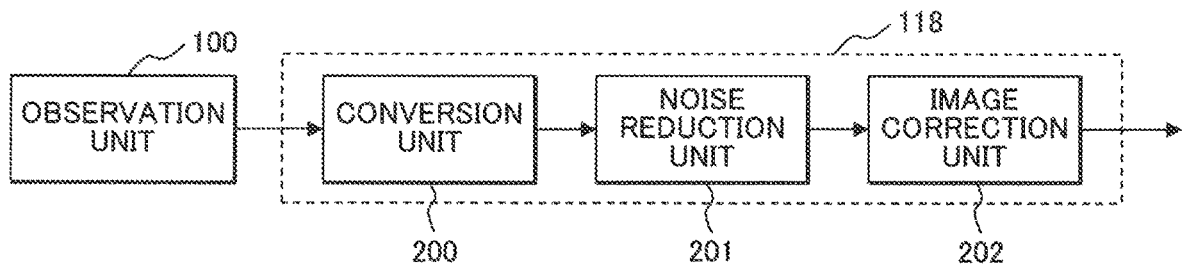
FIG. 2 is a drawing illustrating one example of a configuration of an image processing unit according to an example 1.

Next, a processing content of the image processing unit 118 of the MRI device illustrated in FIG. 1 will be described. FIG. 2 is a functional block diagram illustrating one example of processing performed with the image processing unit 118 in the MRI device according to this example. The image processing unit 118 of this example is configured of a conversion unit 200, a noise reduction unit 201, and an image correction unit 202. The conversion unit 200 converts the observation data observed with the observation unit 100 into an image by Fourier transformation. The noise reduction unit 201 reduces a noise in the observation data converted into the image. The image correction unit 202 performs correction processing that uses visual characteristics of human. The correction processing that uses the visual characteristics of human is, for example, correction processing that uses Retinex theory, and includes, for example, an edge enhancement and a contrast change. The correction processing that uses the visual characteristics of human will be described later.

The noise reduction unit 201 reduces a noise in the image acquired by converting the observation data. Noise reduction processing includes methods, such as a weighted smoothing filter, a bilateral filter, a non-local mean filter, and a guided filter. In this example, noise reduction processing that uses sparsity of an image will be described. The sparsity, that is, thinness of an image indicates a property where an image or coefficients converted with any basis function includes many zero components.

Figure 3:
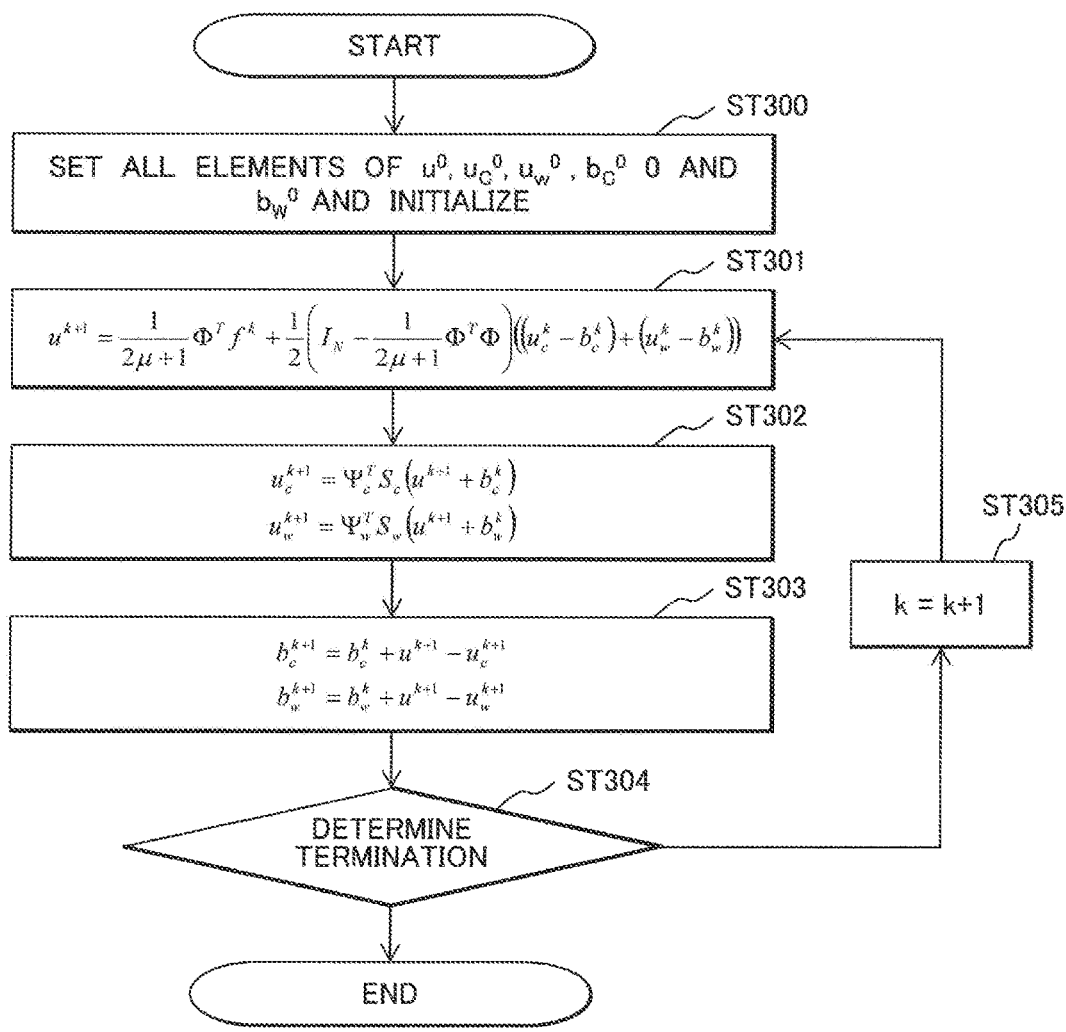
FIG. 3 is a drawing illustrating one example of a processing flow of noise reduction processing according to the example 1.

FIG. 3 is a drawing illustrating one example of processing of the noise reduction unit 201 of this example. As illustrated in FIG. 3, the noise reduction unit 201 performs an initialization at Step ST300, and then, repeatedly executes Steps ST301 to ST305; thus, the noise reduction unit 201 reduces a noise included in the observation data converted into an image.

The following describes the (k+1−th) repetition. At Step ST301, Formula (1) is calculated to obtain an estimation result $u^{k+1}$.

[Expression 1]

$$u^{k+1} = \frac{1}{2\mu+1}\Phi^T f^k + \frac{1}{2}\left(I_N - \frac{1}{2\mu+1}\Phi^T\Phi\right)((u_c^k - b_c^k) + (u_w^k - b_w^k)) \quad (1)$$

Here, $f^k$ indicates a frequency component of an image updated by the immediately preceding (k-th) repetition, $\Phi$ indicates the Fourier transformation, and $\Phi^T$ indicates an inverse transformation of $\Phi$. All the elements of $I_N$ are 1, and $I_N$ has an array in a size identical to that of $f^k$. Additionally, $u_c^k$, $u_w^k$, $b_c^k$, and $b_w^k$ are changing components calculated in the immediately preceding (k-th) repetition. Additionally, p is a positive constant as a parameter.

Next, at Step ST402, $u_c^{k+1}$ and $u_w^{k+1}$ are calculated from Formulae (2) and (3).

[Expression 2]

$$u_c^{k+1} = \psi_c^T S_c(u^{k+1} + b_c^k) \quad (2)$$

[Expression 3]

$$u_w^{k+1} = \psi_w^T S_w(u^{k+1} + b_w^k) \quad (3)$$

Here, $\psi_c^T$ and $\psi_w^T$ are Curvelet inverse transformation and Wavelet inverse transformation, respectively. Here, while Curvelet transformation and Wavelet transformation are used, for example, Total Variation (TV) and Ridgelet transformation may be used besides this. They may be combined and used.

$S_c$ and $S_w$ indicate processing called Soft Shrinkage. $S_c$ and $S_w$ perform processing indicated in Formulae (4) and (5), respectively, on all the elements. Here, $\Phi_c$ and $\psi_w$ are the Curvelet transformation and the Wavelet transformation, respectively. Additionally, $\lambda$ is a constant as a parameter.

[Expression 4]

$$S_c(u^{k+1} + b_c^k) = \begin{cases} \Psi_c(u^{k+1} + b_c^k) - \frac{|\lambda|}{\mu} & \text{if } \Psi_c(u^{k+1} + b_c^k) \geq \frac{|\lambda|}{\mu} \\ \Psi_c(u^{k+1} + b_c^k) + \frac{|\lambda|}{\mu} & \text{if } \Psi_c(u^{k+1} + b_c^k) \leq \frac{|\lambda|}{\mu} \\ 0 & \text{if } |\Psi_c(u^{k+1} + b_c^k)| < \frac{|\lambda|}{\mu} \end{cases} \quad (4)$$

[Expression 5]

$$S_w(u^{k+1} + b_c^k) = \begin{cases} \Psi_w(u^{k+1} + b_w^k) - \frac{|\lambda|}{\mu} & \text{if } \Psi_w(u^{k+1} + b_w^k) \geq \frac{|\lambda|}{\mu} \\ \Psi_w(u^{k+1} + b_w^k) + \frac{|\lambda|}{\mu} & \text{if } \Psi_w(u^{k+1} + b_w^k) \leq \frac{|\lambda|}{\mu} \\ 0 & \text{if } |\Psi_w(u^{k+1} + b_w^k)| < \frac{|\lambda|}{\mu} \end{cases} \quad (5)$$

Next, at Step ST303, $b_c^{k+1}$ and $b_w^{k+1}$ are calculated using Formulae (6) and (7).

[Expression 6]

$$b_c^{k+1} = b_c^k + u^{k+1} - u_c^{k+1} \quad (6)$$

[Expression 7]

$$b_w^{k+1} = b_w^k + u^{k+1} - u_w^{k+1} \quad (7)$$

Next, at Step ST304, a termination determination is made. The termination determination determines a termination when, for example, the maximum values and a summed value of the changing components u and b fall below specified values, or when the number of repetitions reaches a certain count. Repeatedly executing the above steps reduces the noise in the image as the observation data, which is input from the conversion unit 200. Thus, the noise reduction unit 201 of this example uses the sparsity of the observation data to ensure reducing the noise.

Next, the image correction unit 202 of this example will be described. The image correction unit 202 performs correction processing that uses the visual characteristics of human, that is, a correction of an MRI image based on the visual characteristics of human. In this description, the correction processing that uses the visual characteristics of human means correction processing that uses the Retinex theory in which human eyes have color constancy and brightness constancy that enables the human eyes to sense color and brightness irrespective of illumination light.

Figure 4:
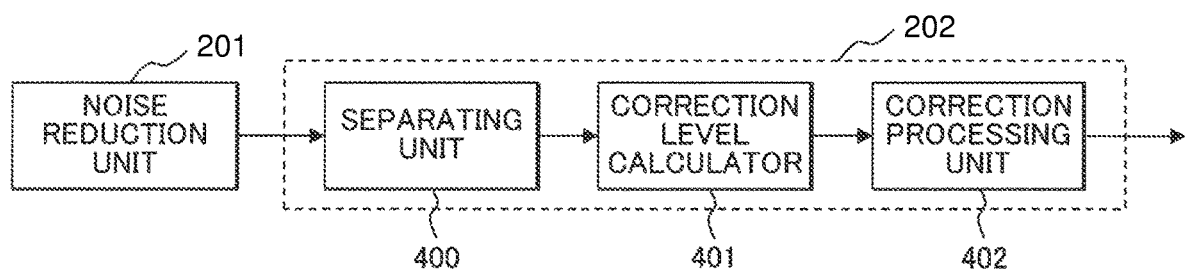
FIG. 4 is a drawing illustrating one example of a configuration of an image correction unit according to the example 1.

FIG. 4 is a drawing illustrating one example of processing of the image correction unit 202 of this example. As illustrated in FIG. 4, the image correction unit 202 is configured of a separating unit 400, a correction level calculator 401, and an image correction unit 402. The separating unit 400 separates a broad luminance component and a local variation component. The correction level calculator 401 calculates correction levels at each position in the input image. The image correction unit 402 corrects the image using each of the calculated components and correction levels.

Processing of each of the separating unit 400, the correction level calculator 401, and the image correction unit 402 will be described. In the separating unit 400, a broad luminance component L is calculated from Formula (8).

[Expression 8]

$$L(x,y) = G(x,y) * I(x,y) \quad (8)$$

In Formula (8), I(x,y) is a noise reduced image input from the noise reduction unit 201, G(x,y) is a blurring function, and * is a convolution operation.

Here, for example, a moving average filter, a Gaussian filter, and a bilateral filter can be used for the blurring function G. While it is described as the convolution operation in Formula (8), convolution processing may be used as a product-sum operation by using the Fourier transformation.

Next, a local variation component R is calculated using Formula (9).

[Expression 9]

$$R(x,y) = \log(I(x,y)/L(x,y)) \quad (9)$$

Next, the correction level calculator 401 will be described. The correction level calculator 401 calculates the correction levels at each position in the input image and generates a correction level map C. For the calculation of the correction level, any one of or combination of a luminance, an inclination, a difference value between the input image and the noise reduced image, an MRI imaging parameter, and the like can be used as an evaluation index. The correction level calculator 401 generates respective correction level maps for the evaluation indexes used for calculating the correction level.

Figure 5:
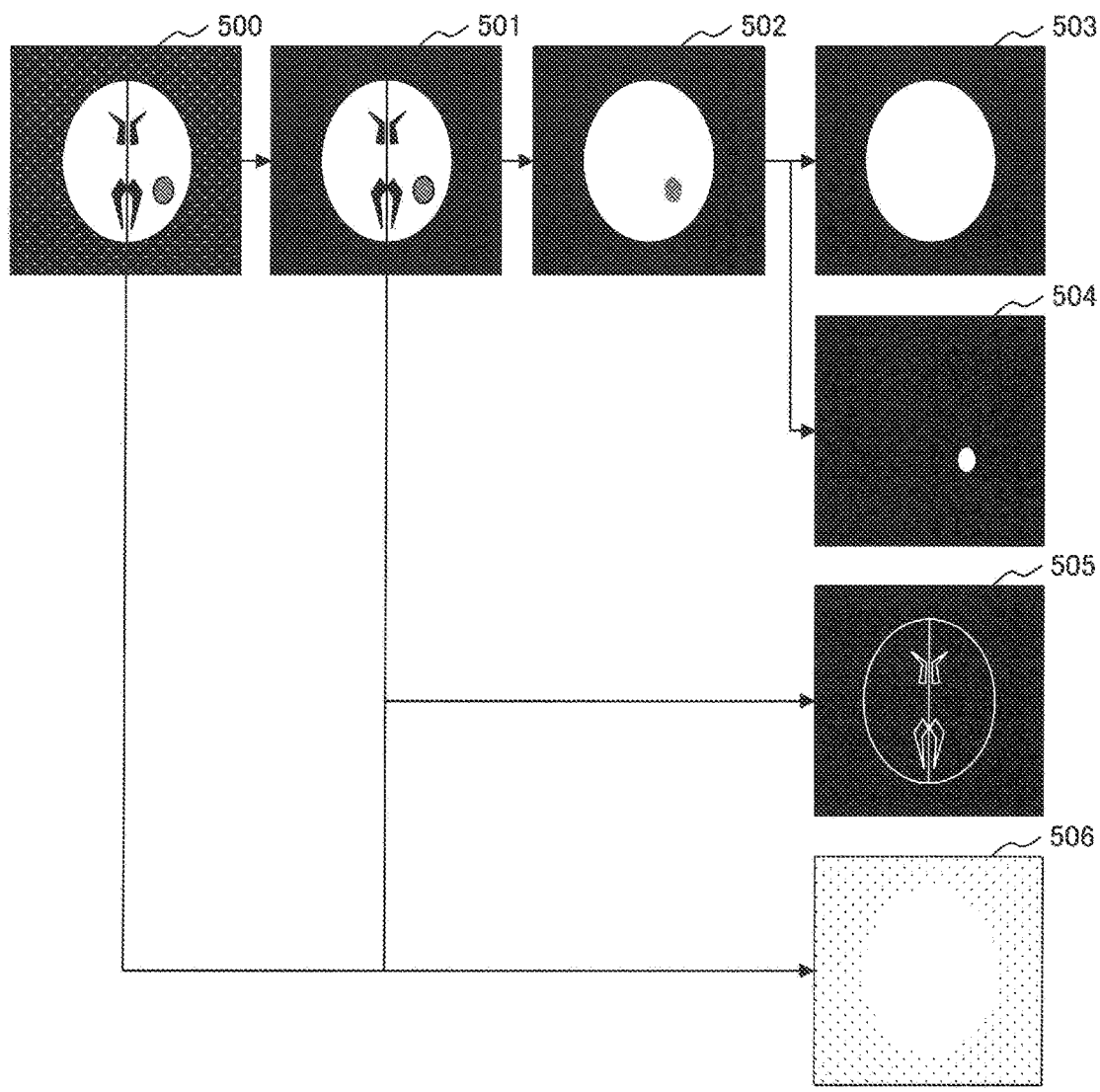
FIG. 5 is a drawing for describing a generation method of a correction level map according to the example 1.

FIG. 5 is a schematic diagram for describing an outline of the correction level map C generated by the correction level calculator 401. Here, an example of using the luminance as the evaluation index is illustrated. In FIG. 5, a noise reduced image 501 calculated with the noise reduction unit 201 is input to the separating unit 400 of the image correction unit 202 based on an observation image 500 into which the observation data is converted with the conversion unit 200 of the image processing unit 118. The separating unit 400 separates the broad luminance component and the local variation component, and thus, a broad luminance component 502 is calculated. The correction level calculator 401, to which this broad luminance component 502 is input, generates a correction level map 503 in order to reduce a noise in a low luminance region, for example. The correction level map 503 uses the luminance, with which the correction level is 0 for a region falling below a predetermined threshold and the correction level is 1 for a region exceeding the predetermined threshold in the broad luminance component 502, as an evaluation index. By setting a luminance range, such as th1 to th2, a luminance range correction level map 504 is calculated. It should be noted that, in FIG. 5, while the correction level has two values of 0 (black) or 1 (white), any value may be used.

When the inclination is used as the evaluation index, the inclination is calculated by, for example, a difference method and a Sobel filter, and then, a large correction level is set for a large inclination region; thus, an inclination correction level map 505 is calculated. It is also possible to calculate a correction level map 506 by calculating a difference value between the observation image 500 and the noise reduced image 501, which are input, as the evaluation index and estimating a region reduced as a noise. Thus, the correction level calculator 401 of this example calculates one or n pieces of the correction level maps 503 to 506. Calculating a plurality of the correction level maps ensures controlling a region to perform a contrast correction and an edge enhancement and intensity of each correction effect. That is, in the device of this example, calculating a plurality of the correction levels based on a plurality of the evaluation indexes in the correction level calculator 401 ensures performing further flexible correction processing.

Next, the correction processing unit 402 will be described. The correction processing unit 402 uses the local variation component R separated by the separating unit 400 and the correction level map C calculated by the correction level calculator 401, and corrects the noise reduced image by Formula (10).

[Expression 10]

$$O(x, y) = I(x, y) + \alpha \cdot R(x, y) \prod_{l=1}^{n} C_l(x, y) \quad (10)$$

Here, O(x,y) is a corrected image corrected by the correction level calculator 401, $C_i(x,y)$ is a calculated correction level map, and $\alpha$ is a positive parameter that controls a correction proportion.

Final correction levels at each of pixel positions are calculated by Formula (10), and the input image is corrected. Here, while the correction level map is multiplied, an addition may be a substitution. Correction can be performed further easily by using the multiplication when the correction level is normalized within a range of 0 to 1 since the final correction level falls within a range of 0 to 1. Configuration of an addition or a polynomial combining the addition and multiplication ensures calculating a further flexible correction level. That is, in the correction processing unit 402 of this example, performing the correction processing by multiplying or adding, or combining adding and multiplying the plurality of correction levels calculated with the correction level calculator 401 ensures a flexible response.

Thus, the image correction unit 202 of this example ensures a further flexible correction level calculation by a configuration including the correction level calculator, which calculates the correction level using the observation data converted into the image in the conversion unit, the noise reduced data output from the noise reduction unit, and the broad luminance component in the noise reduced data, and the correction processing unit, which performs a correction using the observation data, the local variation component in the noise reduced data, and the correction level.

Figure 6:
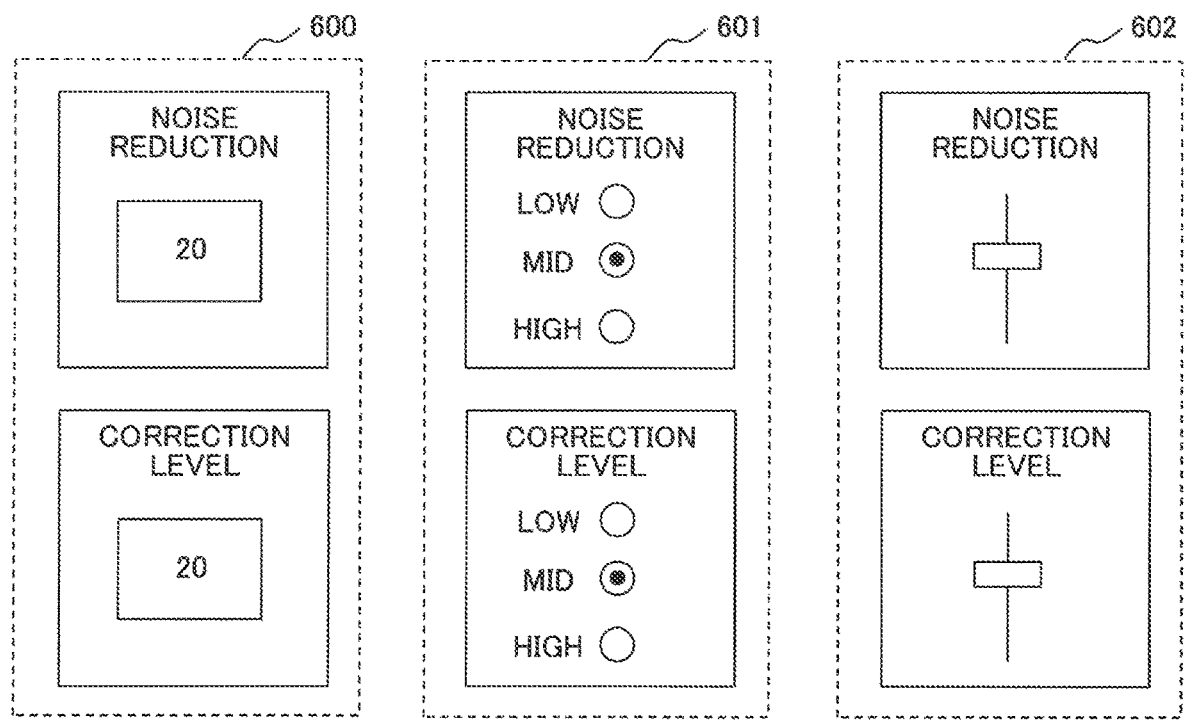
FIG. 6 is a drawing illustrating presentation examples of an input unit according to the example 1.

The configuration of this example causes a user to set the parameter in the noise reduction processing and the correction processing using the input unit 119 of the reconfiguration unit 106. FIG. 6 is one example of screens presented to the user on the input unit 119. As illustrated in FIG. 6, for example, an input 600 with numerical values, an input 601 with radio buttons, and an input 602 with sliders are possible. At this time, it is preferred that some sets of parameters are prepared. It may be configured that the user can select for each imaging site and each imaging mode of the test object.

Figure 7:
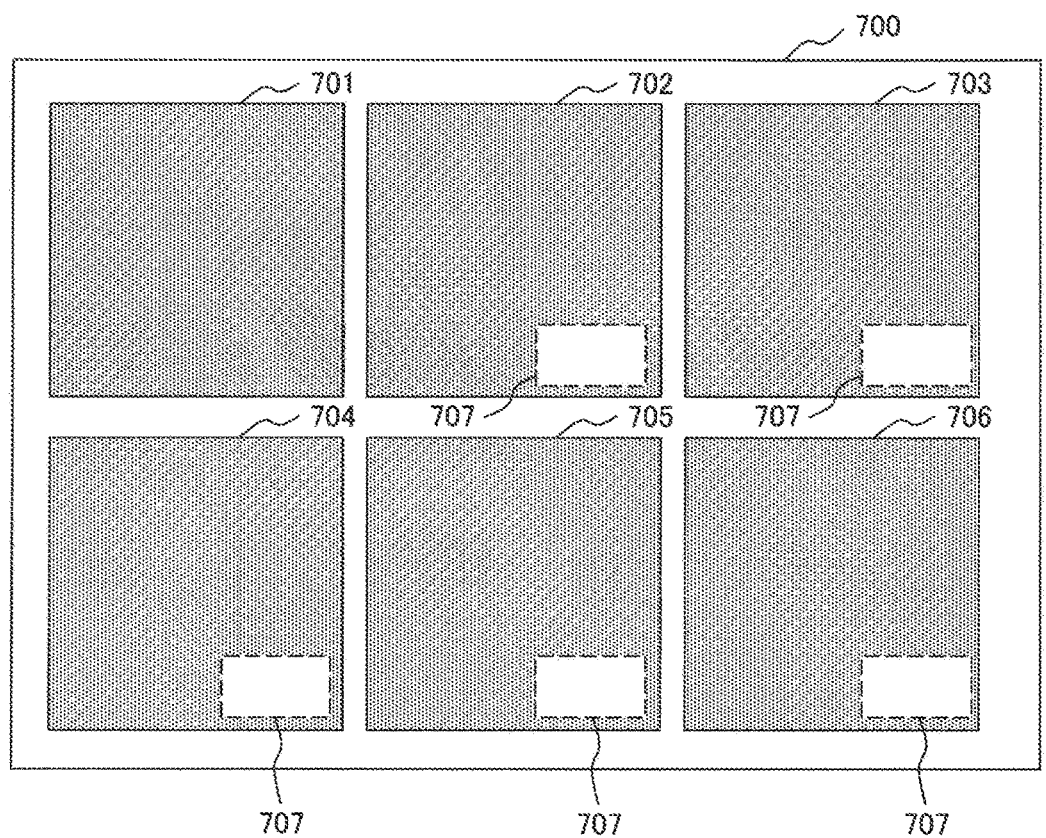
FIG. 7 is a drawing illustrating display examples on a display according to the example 1.

The output unit 120 includes an output device, such as a display, and displays the observation image, the noise reduced image, and the corrected image acquired at the respective functional blocks illustrated in FIG. 2. FIG. 7 is display examples on the output device, such as the display, of the output unit 120. As illustrated in FIG. 7, it may be configured to simultaneously display a plurality of correction results 704 to 706, which are different in combination of the correction level maps and correction processing, as well as an observation image 701, a noise reduced image 702, and a corrected image 703 on an output device 700, such that the user can select. A region 707 that displays a kind of the correction level map, a parameter, and the like used in the processing may be displayed.

As described above, with the configuration of this example, the correction processing that uses the visual characteristics of human ensures rapidly imaging a high-quality MRI image that is competent in the clinical field, thereby ensuring a reduced burden on a patient due to a shortened imaging time based on a reduction in NEX and an improved diagnosis efficiency.

Example 2

An example 2 is an example that ensures the user easily acquiring preferred images by controlling a noise removal and correction using various kinds of parameters of the MRI device. That is, this example is an example of a diagnostic imaging device and an image acquisition method configured to include a noise reduction unit that reduces a noise in observation data converted into an image, a separating unit that separates a broad luminance component and a local variation component from the noise reduced data acquired with the noise reduction unit, a correction level calculator that calculates a correction level using the observation data, the noise reduced data, and the broad luminance component, a correction processing unit that performs a correction using the observation data, the local variation component, and the correction level, and a correction control unit that uses parameters at a time of an acquisition of the observation data to control the noise reduction unit, the correction level calculator, and the correction processing unit.

Also in this example, an overall configuration of the MRI device is illustrated in FIG. 1 similarly to the example 1. This example differs from the example 1 in that an observation parameter of the observation unit 100 is used in the noise reduction unit 201 and the image correction unit 202 for performing the correction processing that uses the visual characteristics of human.

Figure 8:
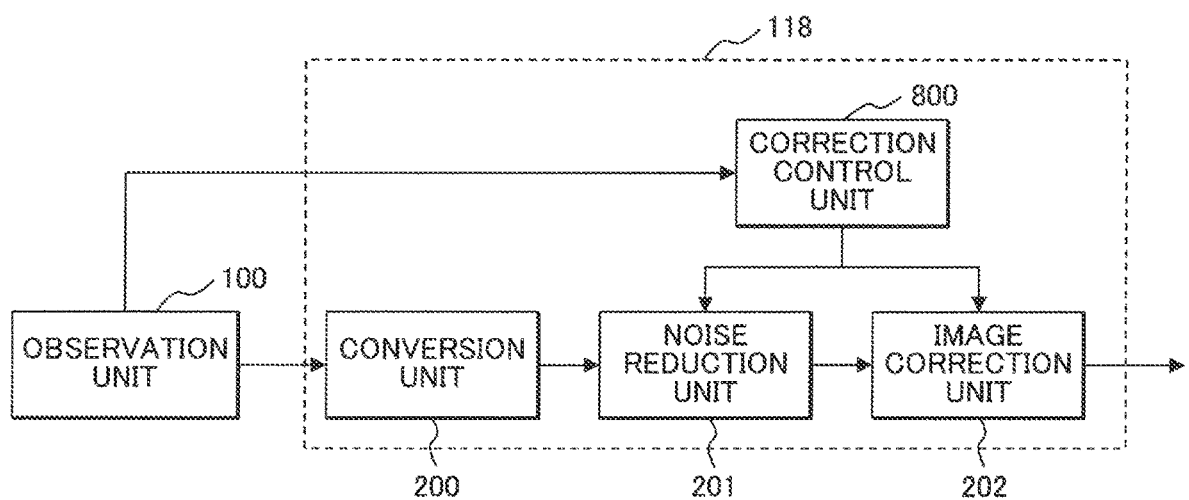
FIG. 8 is a drawing illustrating one example of a configuration of an image processing unit according to an example 2.

FIG. 8 is a block diagram illustrating one example of a main part configuration in the example 2. In the example 2, a correction control unit 700 that controls the noise reduction unit 201 and the image correction unit 202 is added in the image processing unit 118.

The correction control unit 800 will be described. Parameter information used at the observation is input to the correction control unit 800 from the observation unit 100. The parameter information used at the observation includes, for example, a Repetition Time (TR) of the MRI device, a flip angle, a slice thickness, a Field of View (FOV), a matrix size, the NEX of signals, which is the number of multiple imaging and adding, a band width, and site information. In the MRI device, these parameters change the SNR; therefore, performing appropriate noise reduction and correction using these parameters ensures the user easily acquiring a further preferable image. For example, when the NEX is low, it is expected that the SNR decreases. Therefore, it is necessary to increase the noise reduction effect and the correction effect. The correction control unit 800 calculates appropriate noise reduction and correction parameters from the above-described parameters, and then, transmits the respective parameters to the noise reduction unit 201 and the image correction unit 202.

First, the parameters transmitted to the noise reduction unit 201 are the parameter p used in Formula (1) and the parameter λ used in Formulae (4) and (5). The SNR typically decreases when the TR is short, when the flip angle is small, when the slice pressure is thin, when the FOV is small, when the matrix size is large, when the NEX is low, and when the band width is wide. Actually, it is preferred to determine a final correction parameter using a combination of these. It is also possible to prepare a table of the correction parameters with respect to these parameters, store the table in the storage unit of the CPU 108 and the storage device 121 of the reconfiguration unit 106, and then, use the table. When the SNR is expected to decrease, the correction control unit 800 can improve the noise reduction effect by increasing the parameter A and the parameter μ.

On the other hand, the parameters transmitted from the correction control unit 800 to the image correction unit 202 are two, a parameter for calculating correction level map and a correction processing parameter. For the parameter for calculating correction level map, for example, a threshold value, a width of luminance, and correction level information for each of them are transmitted. That is, a luminance range necessary in the clinical field is defined in advance using mode information and site information in the MRI imaging and the defined correction parameter is calculated; thus, a further preferable correction is performed. For example, in the MRI image, when the luminance of the observation target is roughly within the range of th1 to th2, th1 and th2 are transmitted to the correction level calculator 401, and thus, the correction level map is generated. The generated correction level map includes a luminance range correction level map using th1 and th2 and an inclination correction level map using inclinations near th1 and th2.

The correction processing parameter is the parameter a used in Formula (10). The correction processing parameter a is transmitted to the correction processing unit 402 of the image correction unit 202. As described before, when the SNR decreases, the noise reduction effect increases. This possibly causes necessary edge information to be blurred. Corresponding to this, the correction control unit 800 increases the correction processing parameter a, and thus, the correction is further intensely executed, thereby ensuring acquiring a preferable image.

As described above, with this example, the user can further easily acquire a preferable MRI image using the various kinds of parameters of the MRI device.

Example 3

An example 3 is an example when a diagnostic imaging device is an ultrasonic diagnostic device.

Figure 9:
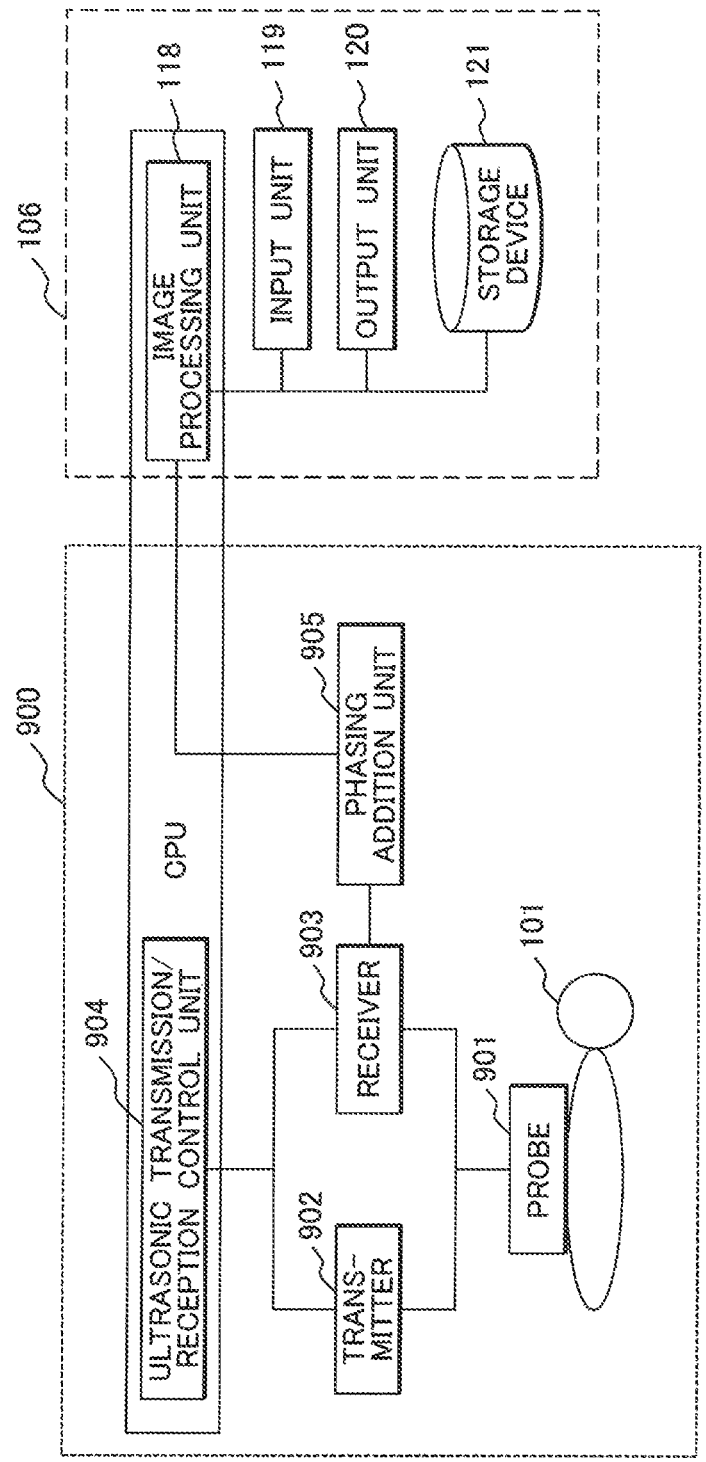
FIG. 9 is a block diagram illustrating one example of an overall configuration of an ultrasonic diagnostic device according to an example 3.

FIG. 9 is a block diagram illustrating one exemplary configuration of an ultrasonic diagnostic device as a medical diagnostic imaging device. In FIG. 9, components identical to configuration components illustrated in FIG. 1 are denoted by identical reference numerals, and thus, the description is omitted. In the same drawing, an ultrasonic observation unit 900 that configures the ultrasonic diagnostic device is configured of an ultrasonic probe 901, a transmitter 902, a receiver 903, an ultrasonic transmission/reception control unit 904, and a phasing addition unit 905.

The transmitter 902 repeatedly transmits an ultrasonic sound wave via the ultrasonic probe 901 to the test object 101 with a time interval. The receiver 903 receives reflected echo signals in time series generated by the test object 101. The ultrasonic transmission/reception control unit 904 controls the transmitter 902 and the receiver 903. The phasing addition unit 905 phases and adds the received reflected echo signals to generate frame data of RF signals in time series. The phasing addition unit 905 includes a built-in analog/digital (A/D) converter and outputs the RF signal frame data as the observation data to the image processing unit 118 of the reconfiguration unit 106. The image processing unit 118 uses the observation data made of the RF frame data to generate an ultrasonic echo image.

The ultrasonic observation unit 900 of this example transmits the observation data to the image processing unit 118. The image processing unit 118 in this example is also illustrated in FIG. 2 similarly to the first and the second examples. However, in this example, the conversion unit 200 of the image processing unit 118 converts the RF frame data into an image. The correction processing correction processing that uses the visual characteristics of human described in the example 1 or the example 2 is performed on the converted image, and thus, a high-quality ultrasonic image can be calculated.

The ultrasonic diagnostic device of this example ensures acquiring the high-quality ultrasonic image.

Example 4

An example 4 is an example of a computed tomography device with which a diagnostic imaging device can acquire a high-quality Computed Tomography (CT) image.

Figure 10:
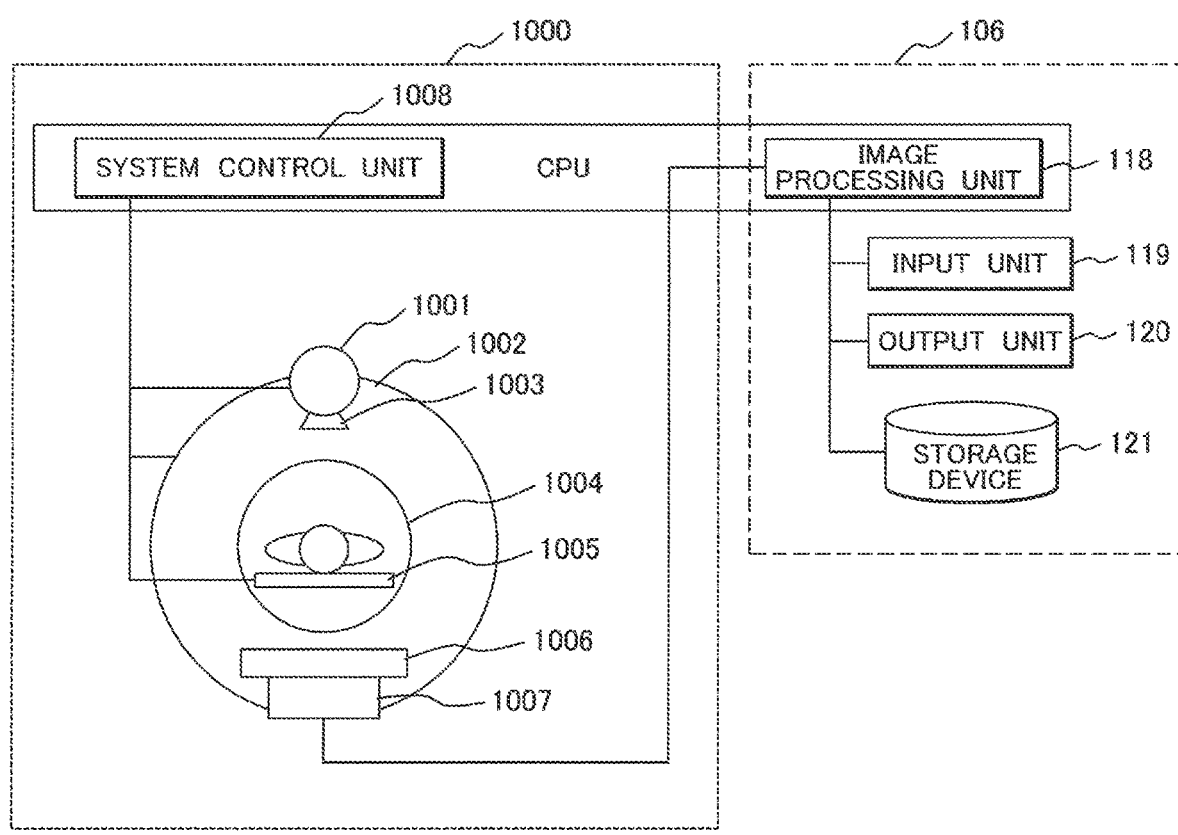
FIG. 10 is a block diagram illustrating one example of an overall configuration of a computed tomography device according to an example 4.

FIG. 10 is a block diagram illustrating one exemplary configuration of a Computed Tomography (CT) device as a medical diagnostic imaging device. In the same drawing, components identical to configuration components illustrated in FIG. 1 are denoted by identical reference numerals, and thus, the description is omitted In FIG. 10, a CT observation unit 1000 is configured of an X-ray tube assembly 1001, a rotating disk 1002, a collimator 1003, an X-ray detector 1006, a data collecting device 1007, a bed 1005, and a system control unit 1008. The X-ray tube assembly 1001 is a device that irradiates a test object placed on the bed 1005 with an X-ray. The collimator 1003 is a device that restricts a radiation range of the X-ray emitted from the X-ray tube assembly 1001. The rotating disk 1002 has an opening 1004 through which the test object placed on the bed 1005 enters, and includes the X-ray tube assembly 1001 and the X-ray detector 1006. The rotating disk 1002 rotates about a peripheral area of the test object.

The X-ray detector 1006 is a device that is disposed opposing the X-ray tube assembly 1001 and measures a spatial distribution of a transmission X-ray by detecting an X-ray transmitted through the test object. The X-ray detector 1006 is a large number of X-ray detecting elements arranged in a rotating direction of the rotating disk 1002 or bidimensionally arranged in the rotating direction and a rotation shaft direction of the rotating disk 1002. The data collecting device 1007 is a device that collects an X-ray dosage detected by the X-ray detector 1006 as digital data. The system control unit 1008 controls, for example, the rotation of the rotating disk 1002, the movement of the bed 1005 in up, down, front, back, right, and left directions, and an electric power input to the X-ray tube assembly 1001.

The CT observation unit 1000 of the computed tomography device of this example transmits the observation data to the image processing unit 118 of the reconfiguration unit 106. The image processing unit 118 in this example is also illustrated in FIG. 2 similarly to the first and the second examples. However, in this example, the conversion unit 200 converts the observation data into an image by processing, such as a filtered back projection method and successive approximation image reconfiguration method. The correction processing that uses the visual characteristics of human described in the example 1 or the example 2 is performed on the converted image, and thus, a high-quality CT image can be calculated.

As described above, this example ensures acquiring the high-quality CT image. Furthermore, it is possible to reduce the X-ray dosage compared with a conventional manner, and thus, a reduced radiation exposure is expected.

It should be noted that the present invention is not limited to the above-described examples, and various modifications are included. For example, the above-described examples are described in detail for better understanding of the present invention, and are not intended to limit to necessarily include every configuration described. A part of a configuration of a certain example can be replaced with a configuration of another example, and a configuration of another example can be added to a configuration of a certain example. A part of configurations of each example can be subjected to an addition of another configuration, removal, and replacement.

Furthermore, while it has been described an example of generating a CPU program that achieves a part or all of each of the above-described configurations, functions, processing units, and the like, it is needless to say that a part or all of them may be achieved by hardware, for example, by designing with an integrated circuit.

REFERENCE SIGNS LIST

100 . . . observation unit,
101 . . . test object,
102 . . . static magnetic field generation system,
103 . . . gradient magnetic field generation system,
104 . . . transmission system,
105 . . . reception system,
106 . . . reconfiguration unit,
107 . . . sequencer,
108 . . . central processing unit (CPU),
109 . . . gradient magnetic field coil,
110 . . . gradient magnetic field power source,
111 . . . high frequency generator,
112 . . . modulator,
113, 115 . . . amplifier,
114 . . . high frequency coil,
116 . . . quadrature phase detector,
117 . . . analog/digital (A/D) converter,
118 . . . image processing unit,
119 . . . input unit,
120 . . . output unit,
121 . . . storage device,
200 . . . conversion unit,
201 . . . noise reduction unit,
202 . . . image correction unit,
400 . . . separating unit,
401 . . . correction level calculator,
402 . . . correction processing unit,
500 . . . observation image,
501 . . . noise reduced image,
502 . . . broad luminance component,
503 to 505 . . . correction level map,
600 . . . input with numerical value,
601 . . . input with radio button,
602 . . . input with slider,
700 . . . display device,
701 . . . observation image,
702 . . . noise reduced image,
703 . . . corrected image,
704 to 706 . . . noise reduced image or corrected image,
707 . . . display region,
800 . . . correction control unit,
900 . . . ultrasonic observation unit,
901 . . . probe,
902 . . . transmitter,
903 . . . receiver,
904 . . . ultrasonic transmission/reception control unit,
905 . . . phasing addition unit,
1000 . . . CT observation unit,
1001 . . . X-ray tube assembly,
1002 . . . rotating disk,
1003 . . . collimator,
1004 . . . opening,
1005 . . . bed,
1006 . . . X-ray detector,
1007 . . . data collecting device, and
1008 . . . system control unit.

The invention claimed is:

1. A diagnostic imaging device comprising:
a noise reduction unit that reduces a noise in observation data converted into an image;
an image correction unit that performs correction processing on noise reduced data acquired with the noise reduction unit, the correction processing using visual characteristics of human; and
an image correction unit that includes a correction level calculator that calculates a correction level using the observation data, the noise reduced data, and a broad luminance component in the noise reduced data.

2. The diagnostic imaging device according to claim 1, wherein the image correction unit further includes a correction processing unit that performs a correction using the observation data, a local variation component in the noise reduced data, and the correction level.

3. The diagnostic imaging device according to claim 2, wherein the correction processing unit integrates a plurality of the correction levels to perform correction processing.

4. The diagnostic imaging device according to claim 2, wherein in the noise reduction unit, a noise is reduced using sparsity of the observation data.

5. The diagnostic imaging device according to claim 1, wherein the correction level calculator calculates a plurality of the correction levels based on a plurality of evaluation indexes.

6. The diagnostic imaging device according to claim 1, wherein the observation data is data acquired with a nuclear magnetic resonance imaging (hereinafter referred to as MRI) device.

7. A diagnostic imaging device comprising:
a noise reduction unit that reduces a noise in observation data converted into an image;
a separating unit that separates a broad luminance component and a local variation component from the noise reduced data acquired with the noise reduction unit;

a correction level calculator that calculates a correction level using the observation data, the noise reduced data, and the broad luminance component;

a correction processing unit that performs a correction using the observation data, the local variation component, and the correction level; and a correction control unit that uses parameters at a time of an acquisition of the observation data to control the noise reduction unit, the correction level calculator, and the correction processing unit.

8. The diagnostic imaging device according to claim 7, wherein the correction level calculator calculates a plurality of the correction levels based on a plurality of evaluation indexes.

9. The diagnostic imaging device according to claim 7, wherein the correction processing unit integrates a plurality of the correction levels to perform correction processing.

10. The diagnostic imaging device according to claim 7, wherein in the noise reduction unit, a noise is reduced using sparsity of the observation data.

11. The diagnostic imaging device according to claim 7, wherein the observation data is data acquired with an MRI device.

12. The diagnostic imaging device according to claim 11, wherein the diagnostic imaging device uses a NEX as a parameter used by the correction control unit, the NEX being a count of multiple imaging and adding with the MRI device.

13. An image acquisition method of a diagnostic imaging device, the method performing:

noise reduction processing that reduces a noise from acquired observation data;

separation processing that separates a broad luminance component and a local variation component from noise reduced data acquired in the noise reduction processing;

correction level calculation processing that calculates a correction level using the observation data, the noise reduced data, and the broad luminance component; and correction processing using the observation data, the local variation component, and the correction level.

14. The image acquisition method according to claim 13, further comprising control processing that uses parameters at a time of an acquisition of the observation data to control the noise reduction processing, the correction level calculation processing, and the correction processing.

\* \* \* \* \*